US007648968B2

(12) United States Patent
Kelly

(10) Patent No.: US 7,648,968 B2
(45) Date of Patent: *Jan. 19, 2010

(54) METHODS OF TREATING DERMAL ULCERS USING GLUCANS

(75) Inventor: Graham Edmund Kelly, Northbridge (AU)

(73) Assignee: Novogen Research Pty. Ltd., North Ryde (AU)

(*) Notice: Subject to any disclaimer, the term of this patent is extended or adjusted under 35 U.S.C. 154(b) by 171 days.

This patent is subject to a terminal disclaimer.

(21) Appl. No.: 11/499,904

(22) Filed: Aug. 4, 2006

(65) Prior Publication Data

US 2007/0142320 A1  Jun. 21, 2007

Related U.S. Application Data

(63) Continuation of application No. 10/421,659, filed on Apr. 22, 2003, now abandoned, which is a continuation of application No. 09/643,940, filed on Aug. 23, 2000, now abandoned, which is a continuation of application No. 08/894,773, filed as application No. PCT/AU96/00138 on Mar. 13, 1996, now Pat. No. 6,242,594.

(30) Foreign Application Priority Data

Mar. 13, 1995 (AU) .................................. PN1661

(51) Int. Cl.
| A61K 31/716 | (2006.01) |
| A61K 31/717 | (2006.01) |
| A61K 31/718 | (2006.01) |
| A61K 31/721 | (2006.01) |
| A61K 47/00 | (2006.01) |

(52) U.S. Cl. ............................ 514/54; 514/57; 514/59; 514/60; 514/925; 514/928

(58) Field of Classification Search ................. 514/54, 514/57, 59, 60, 925, 928
See application file for complete search history.

(56) References Cited

U.S. PATENT DOCUMENTS

| 4,728,642 A * | 3/1988 | Pawelchak et al. ............ 514/57 |
| 4,739,046 A | 4/1988 | Di Luzio |
| 4,810,646 A | 3/1989 | Jamas et al. |
| 4,833,131 A | 5/1989 | Williams et al. |
| 4,960,697 A | 10/1990 | Johal et al. |
| 4,973,581 A | 11/1990 | Matsuzaki et al. |
| 4,992,540 A | 2/1991 | Jamas et al. |
| 5,084,386 A | 1/1992 | Tusé et al. |
| 5,238,925 A | 8/1993 | Bentley |
| 5,397,773 A | 3/1995 | Donzis |
| 6,242,594 B1 | 6/2001 | Kelly |

FOREIGN PATENT DOCUMENTS

| AU | B-62296/86 | 7/1990 |
| AU | B-64411/90 | 6/1994 |
| BE | 883444 | 11/1980 |
| EP | 0 682 877 B1 | 4/2003 |
| JP | 55-076817 A | 6/1980 |
| JP | 55-076818 A | 6/1980 |
| JP | 55-078001 A | 6/1980 |
| JP | 59-210901 A | 11/1984 |
| JP | 61-291509 A | 12/1986 |
| JP | 62-205008 A | 9/1987 |
| JP | 63-017828 A | 1/1988 |
| WO | WO 87/01037 A1 | 2/1987 |
| WO | WO 90/12106 A1 | 10/1990 |
| WO | WO 91/03495 A1 | 3/1991 |
| WO | WO 94/04163 A1 | 3/1994 |
| WO | WO 97/46208 A2 | 12/1997 |

OTHER PUBLICATIONS

Derwent Abstract Accession No. 52394 C/30, JP 55-076817 A, Jun. 10, 1980, 1 page.
Derwent Abstract Accession No. 52395 C/30, JP 55-076818 A, Jun. 10, 1980, 1 page.
Derwent Abstract Accession No. 52560 C/30, JP 55-078001 A, Jun. 12, 1980, 1 page.
Derwent Abstract Accession No. 85-015010/03, JP 59-210901 A, Nov. 29, 1984, 2 pages.
Derwent Abstract Accession No. 86381 C/49, B04, BE 883 444 A, Nov. 24, 1980, 1 page.
Derwent Abstract Accession No. 87-033998/05, JP 61-291509 A, Dec. 22, 1986, 1 page.
Derwent Abstract Accession No. 87-294398/42 D16, D17, JP 62-205008 A, Sep. 9, 1987, 1 page.
Duckova, K. et al., "Some results of preclinical and clinical evaluation of topical preparations containing glucan," *Proc. 1st World Meeting APGI/APV*, Budapest, Hungary, pp. 729-730 (1995).
International Search Report for WIPO Appl. No. PCT/AU96/00138, mailed on May 15, 1996, 5 pages.
International Preliminary Examination Report for WIPO Appl. No. PCT/AU96/00138, completed on Mar. 12, 1997, 6 pages.
Supplementary European Search Report for EP Appl. No. EP 96 90 4672, dated Nov. 29, 2000, 3 pages.
Search Report under Section 17 for GB Appl. No. GB 9823767.0, date of search Mar. 3, 1999, 1 page.
Office Action mailed Jun. 23, 1998 for U.S. Patent No. 6,242,594.
Amendments filed Dec. 23, 1998, for U.S. Patent No. 6,242,594.
Office Action mailed Mar. 31, 1999, for U.S. Patent No. 6,242,594.
Amendment filed Sep. 30, 1999, for U.S. Patent No. 6,242,594.
Final Office Action mailed Dec. 23, 1999, for U.S. Patent No. 6,242,594.
Amendment After Final filed Jun. 21, 2000, for U.S. Patent No. 6,242,594.

(Continued)

*Primary Examiner*—Shaojia Ana Jiang
*Assistant Examiner*—Everett White

(57) ABSTRACT

The present invention is directed to methods of using glucan compositions, comprising water insoluble microparticulate glucans, in the treatment of dermal ulcers. The water insoluble microparticulate glucans used in the compositions comprise branched β-(1,3)(1,6) glucan. The glucan compositions used in the present invention are essentially free of unbranched β-(1,3)(1,6) glucan and non-glucan components.

17 Claims, 1 Drawing Sheet

OTHER PUBLICATIONS

Office Action mailed Jun. 19, 2001, for U.S. Appl. No. 09/643,940.
Amendment filed Dec. 19, 2001, for U.S. Appl. No. 09/643,940.
Office Action mailed Mar. 11, 2002, for U.S. Appl. No. 09/643,940.
Amendment filed Aug. 8, 2002, for U.S. Appl. No. 09/643,940.
Office Action mailed Oct. 22, 2002, for U.S. Appl. No. 09/643,940.
Office Action mailed Dec. 8, 2004, for U.S. Appl. No. 10/421,659.
Amendment and Response filed May 6, 2005, for U.S. Appl. No. 10/421,659.
Final Office Action mailed Jul. 26, 2005, for U.S. Appl. No. 10/421,659.
Amendment After Final filed Aug. 31, 2005, for U.S. Appl. No. 10/421,659.
Office Action mailed Feb. 6, 2006, for U.S. Appl. No. 10/421,659.
Response filed May 8, 2006, for U.S. Appl. No. 10/421,659.
Advisory Action mailed Jul. 20, 2006, for U.S. Appl. No. 10/421,659.
Muller et al., Lipid Content of Microparticulate (1→3)-β-D-Glucan Isolated from *Saccharomyces cerevisiae, Microbios* 79, 1994, pp. 253-261.

* cited by examiner

METHODS OF TREATING DERMAL ULCERS USING GLUCANS

This application is a continuation of U.S. application Ser. No. 10/421,659, filed Apr. 22, 2003 now abandoned, which is a continuation of U.S. application Ser. No. 09/643,940, filed Aug. 23, 2000, now abandoned, which is a continuation of U.S. application Ser. No. 08/894,773, filed Dec. 2, 1997, now U.S. Pat. No. 6,242,594, which is a 35 U.S.C. §371 filing of PCT Application PCT/AU96/00138, filed Mar. 13, 1996, which claims priority to Australian Application PN 1661, filed Mar. 13, 1995. All of these applications are incorporated herein by reference in their entirety for any purpose.

FIELD OF INVENTION

The present invention relates to a process for the extraction of a naturally occurring carbohydrate (glucan) from microorganisms as well as the glucan produced by this process. The invention also relates to novel therapeutic uses of glucan.

BACKGROUND TO THE INVENTION

Glucan is a generic term referring to an oligo- or polysaccharide composed predominantly or wholly of the monosaccharide D-glucose. Glucans are widely distributed in nature with many thousands of forms possible as a result of the highly variable manner in which the individual glucose units can be joined (glucosidic linkages) as well as the overall steric shape of the parent molecule.

The glucan referred to in this invention typically is a linear chain of multiple glucopyranose units with a variable number of side-branches of relatively short length. The glucosidic linkages are predominantly (not less than 90%) β-,3 type with a lower number (not greater than 10%) of β-1,6 type linkages; the β-1,3 linkages form the bulk of the backbone of the molecule, while the β-1,6 linkages occur predominantly in the side-branches. The chemical name of this form of glucan is poly-(1,3)-β-D-glucopyranosyl-(1,6)-β-D-glucopyranose. Glucan is a well described molecule.

This form of glucan is found principally in the cell wall of most fungi (including yeasts and moulds) and in some bacteria. Glucan, in combination with other polysaccharides such as mannan and chitin, is responsible for the shape and mechanical strength of the cell wall. The glucan typically accounts for approximately 40% to 50% of the weight of the cell wall in these cells.

The chemical structure of fungal cell wall glucan has been studied in detail, with the following sentinel articles being incorporated herein by reference—Bacon et al (1969); Manners et al (1973).

Fungal cell wall glucans have long been used in industry, particularly the food industry, usually in a semi-purified form. Their uses have included use as stabilizers, binders, thickeners and surface active materials.

It also has been known for some forty years that fungal cell wall glucans are biologically active, exerting a number of effects on the reticuloendothelial and immune systems of animals. The outstanding biological effect in this regard is their ability to stimulate non specifically the activity of the body's primary defence cells—the macrophage and the neutrophil. This is thought to be due to receptors to β-1,3 glucan displayed on the surface of these cells (Czop and Austen, 1985). The interaction between glucan and its receptor producing such stimulatory effects as enhanced phagocytosis (Riggi and Di Luzio, 1961), increased cell size (Patchen and Lotzova, 1980), enhanced cell proliferation (Deimann and Fahimi, 1979), enhanced adherence and chemotactic activity (Niskanen et al, 1978), and production of a wide range of cytokines and leukotrienes (Sherwood et al, 1986, 1987).

The aforementioned biological responses to fungal cell wall glucan have been reported to result in a number of clinical effects including: enhanced resistance to infections with fungi (Williams et al, 1978), bacteria (Williams et al, 1983), viruses (Williams and Di Luzio, 1985), protozoa (Cook et al, 1979) following systemic application: enhanced antitumour activity following systemic application (Williams et al, 1985) or intralesional application (Mansell et al, 1975); and enhanced immune responsiveness following systemic application (Maeda and Chihara, 1973). It will be readily seen that these clinical effects are highly beneficial and important and represent an opportunity to develop novel pharmaceutics based on fungal cell wall glucans, such pharmaceutics having potentially wide application in both veterinary and human medicine.

Of the various fungal cell wall glucans tested, that from the yeast *Saccharomyces cerevisiae* has proven to be acceptable in terms of efficacy and safety as an immune stimulant in animals and humans. Hereinafter this will be referred to as *Saccharomyces cerevisiae* ("Sc")-glucan. Predominantly or wholly β-1,3 glucans from other fungi, bacteria or plants from the Graminaceae family have been shown to be immunostimulatory in animals but compared to Sc-glucan either are not as potent or if they do have comparable or greater potency then that is usually associated with a higher level of undesirable side-effects.

Sc-glucan has been shown to be biologically active as an immune stimulant in animals in various forms. These include (a) a large molecular weight (typically greater than $3\times10^6$ d), water-insoluble, microparticulate form, or (b) smaller molecular weight (typically less than 500,000 d) forms which are dispersible or soluble in water. Water-solubility is described as being achieved either through cleavage of the large microparticulate glucan form to smaller molecules using processes such as enzymatic digestion or vigorous pH adjustments, or by complexing to salts such as amines, sulphates and phosphates. The principal advantage of the smaller, water-soluble form vs the larger microparticulate form is that it is safer when given by parenteral routes of administration such as intravenously. Also, it is likely that the smaller sized molecules are more bio-available on a molar basis.

To date it has neither been technically possible nor economically feasible to synthesise glucan on a commercial basis. Thus preparation of commercial quantities of β-1,3 glucan for therapeutic uses requires that it be extracted from fungi, bacteria, algae or cereal grains.

DESCRIPTION OF THE PRIOR ART

A number of different processes are described for the preparation of Sc-glucan for pharmaceutical use. A common feature of these different processes is the extraction of microparticulate glucan as the primary step; the glucan is either then used in the final therapeutic formulation in that microparticulate form or is further processed to a smaller molecular weight material ("soluble glucan") by modification of its chemical and/or spatial structures.

(i) Microparticulate Glucan

The extraction of Sc-glucan from whole yeast cells depends on the fact that the bulk of the cell wall glucan is insoluble in water, strong alkali, acid and organic solvents whereas all other cell wall components are soluble in one or more of these solutions.

The essential principles of extraction of Sc-glucan are (i) lysis of the yeast cell to allow the intact cell walls to be separated from the less dense cytoplasmic contents, and (ii) subsequent or concomitant dissolution of unwanted wall components such as other carbohydrates (glycogen, mannan, glucosamine), lipids and proteins using various combinations of water, alkali, acid and organic solvents. It is preferred in such processes that the three-dimensional matrix structure of the cell wall remains unaltered and intact as a cell wall skeleton (also known as a "cell sac"), comprised predominantly of β-(1,3)(1,6)-glucan. The cell wall skeletons characteristically are spherical, hollow structures of approximately 4 to 20 u diameter and with a molecular weight of between approximately 1,000,000 to 3,000,000 daltons and they are insoluble in water. This end-product is termed microparticulate Sc-glucan.

A number of methods of extraction of microparticulate Sc-glucan are known, although all are essentially variations of a common method. The described methods entail the following steps.

1. Contact of whole yeast cells with strong alkali solution (pH 12 to 14). This effects lysis of the cells and dissolution of most of the non-glucan components except lipids. This step is uniformly rigorous in all described processes. The contact usually is repeated two to three times using fresh batches of alkali and heat also usually is applied to speed the reaction time.
2. The cells then are exposed to acid (pH 1 to 5) with heat to effect dissolution of certain residual non-glucan components and to effect some hydrolysis of the glycosidic linkages, principally the β-1,6 linkages in the side branches and to a minor extent β-1,3 linkages in the glucan backbone side-branches. The rigour of this step varies considerably between the known processes of relatively mild acid treatment where the conformational changes are minimal and many of the side-branches are retained, through to extensive acid treatment where little or no side-branches remain and which permits hydration of the helical glucan coils during subsequent steps to convert to a water-soluble form.
3. Contact of the cell residue with alcohol and heat with or without additional subsequent exposure to solvents, particularly ether or petroleum ether to effect removal of lipids.

See, for example, Hassid et al (1941), Manners (1973) et al, Di Luzio (1979), and U.S. Pat. Nos. 4,810,694 and 4,992,540.

Prior art methods for the production of microparticulate glucan may be regarded as disadvantageous in one or more respects. These include poor yield (such as less than about 5% w/w), low purity (such as less than about 90% purity), extended processing time, significant waste production, and high cost.

(ii) Soluble Glucan

Microparticulate Sc-glucan is water insoluble due to the tightly bound triple helical carbohydrate coils which resist hydration.

There are two principal purposes to seek to solubilize Sc-glucan. The first reason is the risk of microembolization associated with the injection of microparticulate glucan by intravenous or other parenteral routes. The second reason is that a reduction in molecular weight of the Sc-glucan might reasonably be expected to be associated with increased biological efficacy due to greater bioavailability of the glucan molecules.

Solubilization of microparticulate glucan can be achieved in various ways.

One way is to expose the glucan to a specific enzyme, β-1,3-glucosidase which cuts the long linear chain into shorter lengths. The disadvantage of this method is that the enzymic digestion process is difficult to control and can result in excessive hydrolysis of the glucan molecule to monosaccharides or oligosaccharides which lack immunostimulatory activity.

Another way is to attach charged groups such as phosphate (U.S. Pat. Nos. 4,739,046; 4,761,402), sulphate (Williams et al, 1991) and amine (U.S. Pat. No. 4,707,471) which permit hydration of the molecule. Both phosphorylated (U.S. Pat. No. 4,761,042) and sulphated (Williams et al, 1991) Sc-glucans retain their immunostimulatory activity and are highly water soluble. A disadvantage of these methods is that of an additional step of complexity in processing operations, which may add considerably to overall manufacturing cost.

A third approach to solubilization is by sequential alkali/acid/alkali hydrolysis. This was first demonstrated by Bacon et al (1969) who showed that microparticulate Sc-glucan extracted in the traditional manner by repeated NaOH exposures followed by an acid wash, almost completely dissolved when subsequently exposed to 3% NaOH at 75° C. This phenomenon is described again in PCT/US Application No 90/05041 whereby microparticulate Sc-glucan following exposure to acetic acid or formic acid is exposed to 1N NaOH for one to two hours at 80° C. to 100° C. The resultant glucan is of widely heterogenous molecular weight with a high polydispersity index associated with the presence of glucan molecules varying in size from approximately 5,000 d up to approximately 800,000 d. That patent application describes further purification by diafiltration of the hydrolyzed glucan to isolate glucan molecules of defined molecular weight from the heterogenous molecular weight species produced, and the use of various resins to remove contaminating proteinaceous and lipid components.

The present invention insofar as it is concerned with processes for the production of glucan, whether in microparticulate or non-particulate form ("soluble"), seeks to overcome one or more of the problems/deficiencies of prior art processes for the production of glucan.

In addition, as described hereinafter, this invention is also concerned with novel therapeutic uses of glucan, whether produced by the method herein, or other methods known in the prior art.

SUMMARY OF THE INVENTION

In accordance with a first aspect of this invention there is provided a process for production of β-(1,3)(1,6) glucan from a glucan containing cellular source which comprises the steps of:

(a) extracting glucan containing cells with alkali and heat in order to remove alkali soluble components;
(b) acid extracting the cells obtained from step (a) with an acid and heat to form a suspension;
(c) extracting the suspension obtained from step (b) or recovered hydrolyzed cells with an organic solvent which is non-miscible with water and which has a density greater than that of water and separating the resultant aqueous phase, solvent containing phase and interface so that substantially only the aqueous phase comprising glucan particulate material suspended in water remains;
wherein the extraction with said organic solvent provides separation of glucan subgroups comprising branched β-(1,3)(1,6)-glucan, and essentially unbranched β-(1,3) glucan which is associated with residual non-glucan contaminents; and (d) drying the glucan material from step (c) to give particulate glucan.

In order to produce a soluble glucan, step (d) of the above process is omitted and the pH of the solvent extracted aqueous phase comprising glucan particulate material is raised from an acidic pH, to a basic pH so as to effect solubilization of the glucan particles. This step is carried out at a temperature below about 60° C., preferably between about 2° C. to about 25° C., more preferably between about 2° C. to about 8° C., for a time sufficient to achieve solubilization of the glucan particles. Alternatively, soluble glucan may be prepared by suspending the particulate glucan of step (d) in an aqueous alkali solution so as to effect solubilization of the glucan particles. Temperate conditions are set out above.

The pH of the solubilized glucan may then be adjusted as required to give a pharmaceutical product.

In another aspect this invention is directed to the use of glucan for the manufacture of a medicament for the treatment of skin ulceration or bone fracture or the enhancement of fixation of implanted orthopaedic devices, or the prevention/ treatment of ultraviolet light induced skin damage.

In a further aspect this invention is concerned with a method for the treatment of skin ulceration or bone fracture or the enhancement of fixation of implanted orthopaedic devices, or the prevention/treatment of ultraviolet light induced skin damage, which comprises administering to a subject glucan in association with one or more pharmaceutically or veterinarily acceptable carriers or excipients.

In another aspect this invention is concerned with an agent for the treatment of skin ulceration or bone fracture or the enhancement of fixation of implanted orthopaedic devices, or for the prevention/treatment of ultraviolet light induced skin damage which comprises glucan optionally in associate with one or more pharmaceutically acceptable carriers or excipients.

BRIEF DESCRIPTION OF THE DRAWING

The present invention will now be described, by way of non-limiting example only, with reference to the following drawing.

DETAILED DESCRIPTION OF THE INVENTION

Figure 1:
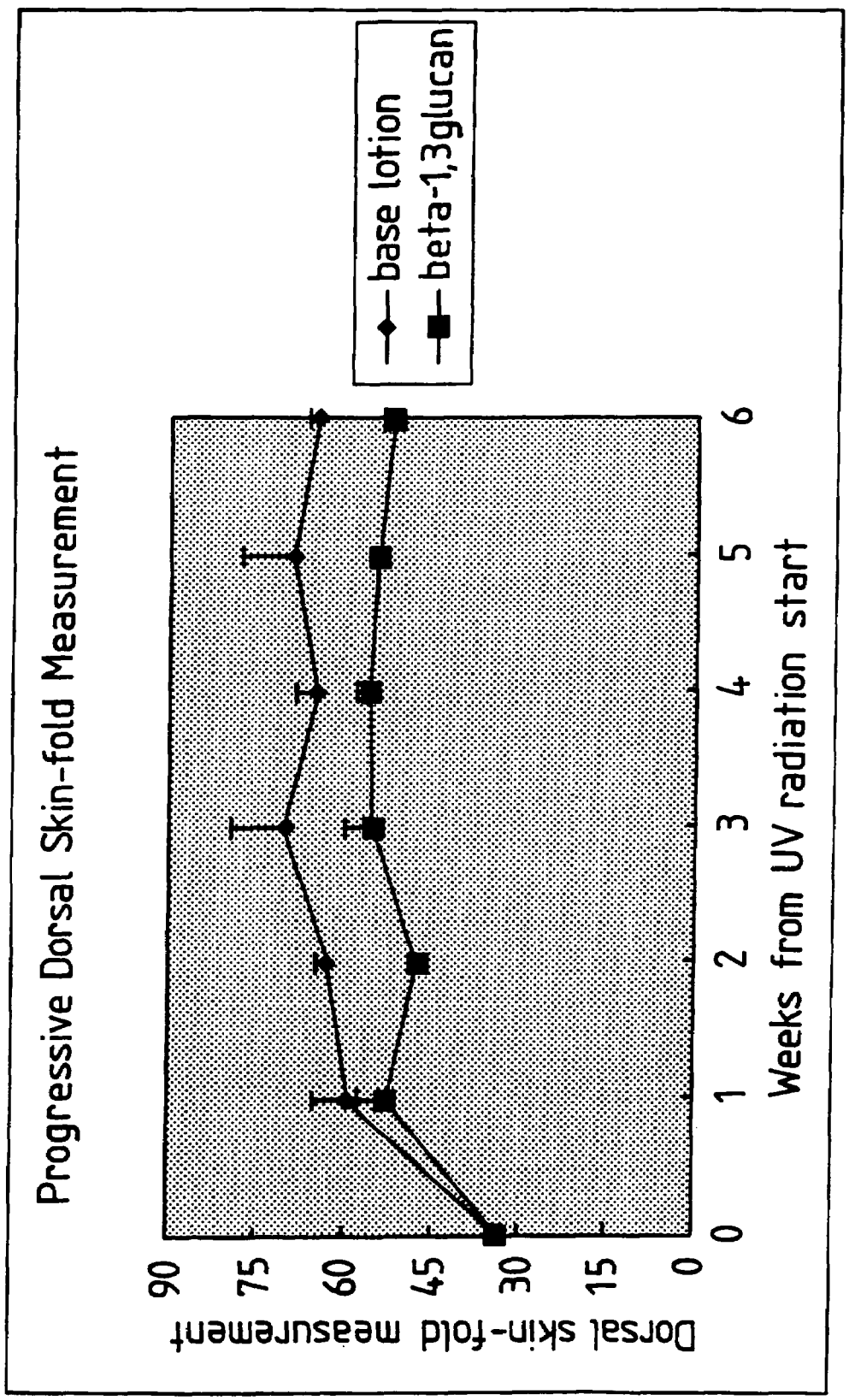
FIG. 1 depicts dorsal skin fold thickness measurements in mice subject to U.V. irradiation over 6 weeks, which mice are treated with glucan (-□-) or treated with a non-glucan base lotion (-◇-).

The process described in detail hereafter sets out the production of $\beta$-(1,3)(1,6) glucan from a cellular glucan source, which is suitable for a variety of pharmaceutical purposes.

In a first aspect the invention is concerned with a process for the production of glucan from a glucan containing cellular source. This process comprises the steps of:
(a) extracting glucan containing cells with alkali and heat, in order to remove alkali soluble components;
(b) acid extracting the cells of step (a) with an acid and heat to form a suspension;
(c) extracting the suspension obtained of step (b) or recovered hydrolyzed cells with an organic solvent which is non-miscible with water and which has a density greater than that of water and separating the resultant aqueous phase, solvent containing phase and interface so that substantially only the aqueous phase comprising glucan particulate material remains;
    wherein the extraction with said organic solvent provides separation of glucan subgroups comprising branched $\beta$-(1,3)(1,6)-glucan, and essentially unbranched $\beta$-(1,3) glucan which is associated with residual non-glucan contaminants: and
(d) drying the glucan material from step (c) to give particulate glucan.

While yeast cells generally and the yeast strain *Saccharomyces cerevisiae* in particular are the preferred source of the glucan according to this invention, any other cells such as fungi or bacteria containing glucan with the properties described herein may be used. A wide range of other yeast and fungal strains can be used in the present process and the following types are included by way of example: *Sclerotium* spp, *Shizophyllum* spp, *Pichia* spp, *Hansenula* spp, *Candida* spp, *Saccharomyces* spp, *Torulopsis* spp.

In the case of *Saccharomyces cerevisiae* the yeast may be grown specifically for the purpose of extraction of Sc-glucan or may be from a commercial source such as yeast manufactured for the baking industry or spent yeast from the brewing industry.

The first step according to the process of the present invention involves treatment of the yeast cells with alkali and heat to effect cytolysis and hydrolysis of the cytoplasmic components and predominant cell wall components including mannan, chitin (glucosamine), proteins and glycogen. This treatment (which may also be referred to as extraction or hydrolysis) releases non-glucan components into the aqueous phase so that they might readily be separated by a process such as centrifugation from the intact cell walls comprising largely glucan. The extent of non-glucan component removal can be readily assessed by standard analytical techniques, such as those described in U.S. Pat. No. 4,992,540.

The alkali extraction step may be carried out in aqueous hydroxide of from about 2% to about 6% concentration (w/v), such as between 3% and 4% (w/v). Sodium hydroxide or potassium hydroxide find particular application because of their availability and relatively low cost. However, any other strong alkali solution which has suitable solubility characteristics, for example, calcium hydroxide or lithium hydroxide, can be used. The yeast is left in contact with the alkali for a time sufficient to remove alkali soluble non-glucan components. Non-glucan components are removed more rapidly at higher temperatures. The digestion may be carried out at temperatures of from about 50° C. to about 120° C., requiring exposure times to the alkali of between fifteen minutes and sixteen hours. During alkali exposure, the process of cytolysis and dissolution of non-glucan components may be facilitated by vigorous mixing of the yeast suspension using appropriate methods such as by example a stirring apparatus or an emulsifying pump.

Repeat exposure of the yeast cells to fresh batches of alkali solution assists in removing non-glucan material, particularly protein, from the disrupted yeast cells. The number of alkali treatments is not limiting on the invention. However, the process should be repeated until it is apparent that the cells have been lysed and the majority, of non-glucan alkali soluble components extracted. This can be confirmed by visual or chemical analysis (such as by gas chromatography/mass spectrometry). Treatments using low strengths of hydroxide solution and low temperatures of alkali exposure generally may require increased numbers of separate alkali exposures. By way of example, alkali treatment may be repeated from one to six times.

In one embodiment of the present invention in relation to the alkali digestion phase, dried commercial *Saccharomyces cerevisiae* is suspended to 10% w/v in sodium hydroxide at a strength of between 3% and 4% and at temperatures of between 80° C. and 100° C. It has been found that three alkali treatments are typically required for a high purity product. Following each separate alkali exposure, the disrupted yeast cells and the supernatant solution are separated by any method which is known to this art including, for example, filtration, centrifugation or chromatography. These separation techniques are referred to by way of example only and are not limiting to the process of the present invention.

The next step in the process involves the exposure of the alkali-insoluble cell wall sacs to acid, generally at a pH from about 2.0 to 6, preferably between 3.5 to 4.5. This procedure dissolves some residual contaminants such as mannan and chitin. However, the principal reason for this step is to induce conformational alterations to the glucan molecule. The principal alteration is a reduction in the number of $\beta$-1,6 side-branches (Table 1). In native cell wall Sc-glucan, the proportions of glycosidic linkages is approximately 90% $\beta$-1,3 and 10% $\beta$-1,6. Acid hydrolysis removes the $\beta$-1,6 side-branches with the degree of hydrolysis being related directly to the vigour of the acid treatment; strong acid treatment (low pH and high temperature, such as pH less than 2 and temperatures above about 100° C. can effectively remove all side-branches whereas less vigorous treatment will leave $\beta$-1,6 linkages in the proportions of between approximately 1% and 8%.

TABLE 1

Effect of acid exposure (phosphoric acid, ph 4.5, 100° C. 30 minutes) on the chemical composition of alkali insoluble Sc-glucan is measured by gas chromatogoraphy-mass spectroscopy.

|  | Pre-acid | Post-acid |
| --- | --- | --- |
| Mannan (% w/w monosaccharides) | 0.5 | 0 |
| $\beta$-glycosidic linkages (mol %): |  |  |
| 1.3 | 54.2 | 94.4 |
| 1.4 | 7.1 | 0 |
| 1.3.4 | 0.7 | 0.2 |
| 1.2.3 | 2.2 | 0.5 |
| 1.3.6 | 5.6 | 2.2 |
| 1.6 | 9.7 | 0 |
| 1.4.6 | 0.8 | 0 |
| 1.2.3.4 | 1.5 | 0 |
| 1.3.4.6 | 1.9 | 0 |
| 1.2.3.6 | 0.4 | 0 |
| Terminal-glc | 6.4 | 2.9 |
| glucitol hexaacetate | 10.8 | 0 |

It is known in the art that the degree of branching of $\beta$-1,3-glucan molecules has an important influence on biological function. For example, it is known that highly branched glucans such as lentinan induce pro-inflammatory effects in addition to immunostimulatory effects and that the pro-inflammatory effects may be associated with adverse clinical side-effects; unbranched Sc-glucans such as those described in U.S. Pat. Nos. 4,739,046. 4,761,402 and 4,7707, 471 or Sc-glucan with reduced branching such as that detailed in PCT/US Patent No. 90/05041 are known to avoid or to greatly diminish pro-inflammatory effects and therefore be more desirable therapeutic agents clinically. Hitherto, however, the structure/function relationship in terms of immunostimulatory capacity and promotion of tissue repair in particular has not been defined. The inventors have defined the optimal degree of branching by comparing the efficacy of differently branched glucan preparations in an animal wound healing model. For example, a full-thickness surgical skin incision may be made in experimental animals such as laboratory rats. Glucan is applied to the wound immediately following wounding and the wound then allowed to heal. Seven days later the degree of healing is tested by determining the amount of force required to separate the apposing wound edges (referred to as 'wound breaking strength'). The results of this experiment are summarised in Table 2. It can be seen that where the degree of branching is measured in terms of the proportion of $\beta$-1,3:$\beta$-1,6 linkages, both a low proportion (90%:10%) as for native glucan and a high proportion (100%: 0%) are less effective in the promotion of dermal wound repair than moderately-branched (98%:2% or 96%:4%) glucan.

TABLE 2

Tensile strength of rat skin wounds (day +7) following application of micro-particulate Sc-glucans with different ratios of $\beta$-1,3 to $\beta$-1,6 glydosidic linkages.

| Treatment | n | $\beta$-1,3:$\beta$-1,6 linkages | Wound tensile strength (g) mean (SD) |
| --- | --- | --- | --- |
| No glucan | 16 | — | 202 (37) |
| Glucan | 8 | 90%:10% | 252 (45) |
| Glucan | 12 | 96%:4% | 358 (49) |
| Glucan | 9 | 98%:2% | 339 (38) |
| Glucan | 10 | 100%:0% | 285 (52) |

1 mg of glucan was applied at a time of operation in oily base to 5 cm long full-thickness incisional wound.

The nature of the acid used in the acid exposure step is generally unimportant. Preferably, the acid is employed to provide a pH of the resultant yeast suspension from about pH 2.0 to about 6.0, more preferably from about pH 3.5 to about 4.5. Suitable acids include hydrochloric, acetic, formic and phosphoric acids.

The process of acid hydrolysis is aided by heating.

The extent of acid treatment, namely pH, temperature and time depends on the degree of $\beta$-1,6 content sought in the glucan product. In order to produce a glucan product generally containing from 2% to 4% $\beta$-1,6 linkages, the pH of the solution is selected to be in the range of about 2 to about 6, temperature is generally between about 50° C. and about 100° C., and the time of reaction from about fifteen minutes to about sixteen hours. The extent of $\beta$-1,6 linkages in the hydrolyzed glucan can be readily determined by standard analytical techniques such as nuclear magnetic resonance (NMR) analysis.

Following the acid exposure stage, the yeast cells predominantly are in the form of isolated cell wall sacs.

In prior art methods of Sc-glucan preparation it has been proposed to expose acid extracted glucan containing cells (cell sacs) with alcohol, petroleum ether or diethyl ether, to selectively dissolve remaining non-glucan components. In contrast, it has been found by the inventors that extracting the acidified glucan containing cells with an organic solvent which is non-miscible with water, that is, has a density greater than 1 g/cm$^3$, is particularly and unexpectedly advantageous. Specifically, a single extraction step with such a solvent provides a fine discrimination between glucan and non-glucan components, and allows ready separation of glucan sub-groups comprising branched glucan containing both $\beta$-1,3 and $\beta$-1,6 linkages (which partitions into the aqueous phase) and which is essentially free of non-glucan components (Table 3), and glucan comprising essentially unbranched $\beta$-1,3 linkages only and which is associated with residual non-glucan membrane components such as chitin and protein (which partitions at the interface between the aqueous and organic phase).

TABLE 3

Effect of chloroform extraction on the chemical composition of alkali/acid treated Sc-glucan.

| | Chemical composition (% w/v) | | | | | |
|---|---|---|---|---|---|---|
| | Glucan | Mannan | Protein | Chitin | Glycogen | Lipids |
| Pre-chloroform treatment | 85.5 | 0.5 | 1.4 | 2.1 | 4.3 | 5.6 |
| Post-chloroform treatment | 98.5 | <0.1 | 0.3 | 0.2 | 0.4 | — |

The branched β-(1,3)(1,6) glucan subgroup which partitions into the aqueous phase may contain minor or trace amounts of unbranched β-1,3 glucan (less than about 5%, generally less than about 2%, more specifically less than about 0.5% (w/w)) and trace amounts of non-glucan contaminants. It may thus be regarded as essentially branched β-(1,3)(1,6) glucan which is free of other glucan and non-glucan components. The unbranched β-(1,3) glucan subgroup which is associated with non-glucan contaminants and which partitions into the interface between the aqueous phase and organic phase can be readily removed. It may contain very minor or trace amounts of branched β-(1,3)(1,6) glucan (generally less than about 1.3% (w/w)) and hence is considered to be essentially unbranched.

Unbranched β-(1,3) glucan may comprise up to 20% of total glucan content (w/w) following alkali/acid/solvent treatment, the remainder comprising branched β-(1,3)(1,6) glucan.

Branched β-(1,3)(1,6) glucan is the most potent biologically active form of glucan in terms of wound healing as shown in Table 4.

TABLE 4

Tensile strength of rat skin wounds (day +7) following application of Sc-glucans recovered from either the aqueous or interface phase following chloroform extraction.

| Treatment | n | Post-chloroform phase | Wound tensile strength (g) mean (SD) |
|---|---|---|---|
| No glucan | 12 | — | 185 (21) |
| Glucan | 14 | Aqueous | 345 (57) |
| Glucan | 8 | Interface | 267 (59) |

Thus it can be readily appreciated, particularly in terms of efficacy of promotion of dermal wound healing and the production of pure glucan molecules, that there is much potential therapeutic benefit in separating the two glucan sub-groups by chloroform extraction (representative of solvents having a density greater than 1).

Solvents which may be used include chloroform ($\delta=1.48$ g/cm$^3$), methylchloroform ($\delta=1.33$), tetrachloroethane ($\delta=1.5953$ g/cm$^3$), dichloromethane ($\delta=1.325$), and carbon tetrachloride ($\delta=595$ g/cm$^3$). Preferably the solvent is volatile to allow ease of removal of any residual. Chloroform is particularly preferred.

For convenience of description the description hereafter will refer to the use of the preferred solvent chloroform. The invention is not so limited, and any solvent having the requisite density may be used in the invention.

The chloroform extraction may be performed in the following manner. The acidified aqueous suspension containing microparticulate glucan may be reacted directly with chloroform in the approximate ratio of chloroform:aqueous cell suspension of between 1:10 and 5:1, preferably 1:4. The yeast cells may comprise (by volume) between about 1% and about 90% of the aqueous suspension, such as between about 30% and 50%. It has been found that the process of extraction with chloroform is not facilitated by heat and preferably is carried out at room temperature. The chloroform and aqueous phases are mixed vigorously using standard methods including, for example, stirring apparatuses or an emulsifying pump so as to effect good contact between the chloroform micelles and the yeast cells. The duration of mixing is a function of the volume of the suspension and the stirring or mixing capacity of the stirring or mixing apparatus. An example by way of illustration is that an emulsifying pump with a pumping capacity of 100 L per minute would be required to mix a suspension volume of 500 L for about ten minutes.

A notable feature of the chloroform extraction step is that the yeast material changes nature both in colour (converting from a light-gray colour to a white colour) and in form (converting from a material with typical cellular characteristics (cell sacs) in suspension to a flocculent particulate material). The bleaching and flocculating effects observed as a result of contact with chloroform (and other solvents having the requisite density referred to above), have not been observed with other organic solvents which have a density less than 1 g/cm$^3$. Solvents which have been tested in this regard include acetone, diethyl ether, petroleum ether, methylene dichloride, ethyl acetate, ethanol, methanol and butanol.

Following chloroform exposure and mixing such as between about five and ten minutes, the suspension is allowed to settle and quickly separates into three distinct phases—a lower organic phase, an upper aqueous phase, and an interface between those two phases which is coloured gray. The three phases are well differentiated and readily separated. The organic phase is slightly opaque and contains lipids but no glucan. The aqueous phase contains glucan particles suspended in water. The interface contains a mixture of glucan, protein, and chitin and lipids. When analyzed by NMR, the glucan in the aqueous phase contains a mixture of β-1,3 and β-1,6 glycosidic linkages in the approximate ratio of 95% to 98%:2% to 5% respectively. The glucan in the interface phase contains predominantly unbranched β-1,3 glycosidic linkages (generally 98 to 100% β-1,3:0% to 2% β-1,6. Effective separation of branched β-1,3 glucan unbranched glucan and non-glucan contaminants is achieved.

This separation of glucan particles based on their level of non-glucan contaminants has been found only with solvents having the density mentioned above, and not with other commonly available organic solvents having a density less than 1 g/cm$^3$. Without being bound by any particular theory the fine discrimination in separating glucan species as exemplified by chloroform, may be due to the combination of lipophilic nature of the solvents and their specific density. This may allow differential separation by weight of cell wall glucan molecules which are associated with other carbohydrates and non-carbohydrates. The glucan and non-glucan molecules in this interface phase can be separated subsequently by evaporation of the chloroform followed by contact of the residue with ether and ethanol to effect dissolution of the non-glucan component, leaving essentially unbranched β-1,3 glucan.

The aqueous glucan suspension collected following the specific solvent exposure step may be boiled briefly to effect complete removal of any residual solvent and the glucan particles then dried by standard methods including for example, freeze-drying, heating, air-drying or spray-drying. The final product is a slightly off-white, flocculent powder comprising particles of Sc-glucan with a diameter typically of between about 1 u up to 10 u with a median diameter of about 3 u (such particles may be referred to as microparticulate glucan). The powder may be milled using standard procedures (hammer milling or ball milling) to give particles of desired size.

The separation of predominantly branched and uncontaminated glucan, from relatively unbranched glucan associated with non glucan components, is not achieved where glucan particles are reacted with alcohol prior to reaction with a solvent have density greater than 1, such as chloroform. This is an unexpected finding.

Prior art description of the use of organic solvents to remove lipids from particulate glucan preparations failed to appreciate the discriminating effects of solvents having a density greater than 1 in separating predominantly branched, uncontaminated glucan from predominantly unbranched contaminated glucan. This invention may thus be regarded as a selection which confers substantial advantage as discussed above.

The microparticulate Sc-glucan produced by this process can be used as a therapeutic in this form. Some examples of use are application for repair of tissues such as skin and bone and bowel where the microparticulate Sc-glucan is applied in formulations such as a powder or cream or lotion or can be used in wound dressings such as bandages or hydrocolloid dressings. Conventional topical formulations may be utilized as are well known in the art and described hereafter.

The process of the invention described above gives rise to a high purity product, having a highly potent bioactivity (as it may comprise glucan having only $\beta$-1,3 and $\beta$-1,6 linkages) which is achieved with short processing time, and high yield. Table 5 demonstrates this by comparing glucan produced according to this invention with glucan prepared according to the procedures of Hassid et al (1941), Di Luzio et al (1979), Manners et al (1973), and Jamas (U.S. Pat. No. 4,992,540).

erally at 75° C. or greater) in the presence of alkali (Bacon et al 1969). In another proposal, the particulate glucan was treated with strong acid (90% formic acid) prior to exposure to alkali and heat. These approaches suffer from a number of disadvantages which include the production of heterogenous glucan products of wide polydispersity which are unsuitable for pharmaceutical use without size fractionation, relative inconvenience, high cost, and production of waste materials.

It has been found by the inventors that the glucan purified as described above is readily solubilised in alkali at low temperatures (particularly between about 2° C. and about 8° C.). In the present invention, solvent extraction of acid treated cell wall sacs with a solvent which has a density greater than 1, where glucan partitioning takes place with subsequent separation and isolation of branched glucans, enables solubilisation in alkali at low temperatures. It is otherwise not possible to produce soluble glucan having the properties described hereafter.

In order to produce soluble glucan, step (d) of the process described above may be omitted and the pH of the solvent extracted aqueous phase comprising glucan particulate material may be raised from an acidic pH to a basic pH so as to effect solubilization of the glucan particles. This step is carried out at a temperature below 60° C., preferably from about 2° C. to about 25° C., more preferably from about 2° C. to about 8° C. for a time sufficient to achieve solubilization of the glucan particles. Alternatively, soluble glucan may be prepared from glucan of step (d) of the above process by reacting the particulate glucan with an aqueous alkali solution so as to effect solubilization of the glucan particles. Temperature conditions are again below 60° C., as specified above.

An unexpected consequence of the present invention is that after alkali solubilisation a glucan material having a small polydispersity index (generally less than about 5, more particularly less than about 3) results. This is highly desirable for

TABLE 5

Comparison of four standard methods of extraction of microparticulate Sc-glucan.

| Method | Processing Time (days) | Glucan Yield % | Component levels (% w/w) | | | | |
|---|---|---|---|---|---|---|---|
| | | | Glucan | Mannan | Glycogen | Protein | Chitin |
| Hassid et al | 8 | 7.8 | 91.7 | 0.4 | 4.5 | 2.9 | 0.4 |
| Di Luzio et al | 12 | 2.0 | 98.1 | 0.3 | 0.5 | 0.7 | 0.2 |
| Manners et al | 18 | 12.1 | 73.8 | 2.0 | 9.8 | 8.6 | 5.8 |
| Jamas et al | 2 | 7.4 | 94.6 | 0.3 | 3.1 | 0.8 | 1.1 |
| The present invention | 2 | 7.7 | 98.5 | <0.1 | 0.4 | 0.3 | 0.2 |

The process of this invention also provides for the conversion of particulate glucan to glucan molecules of smaller molecular weight in the form of a solution, dispersion or colloid, or gel which would be suitable for pharmaceutical, such as parenteral use. Such material may show enhanced bioactivity through the greater availability of glucan ligands for cytophilic glucan receptors. These glucan preparations may be regarded as providing glucan in a soluble form, where glucan particles dissolve in the aqueous phase to give a visually clear solution, or are otherwise hydrated to the extent that they form a dispersion or colloid, or are in the form of a gel. For convenience, these forms may be referred to as soluble glucan.

In the prior art it has been proposed to convert particulate glucan to soluble glucan using rigorous heat treatment (genpharmaceutical agents. Furthermore, no additional size fractionation steps are required. This is contrary to prior art teachings as set out above.

In one embodiment, microparticulate glucan isolated as described above may be suspended in NaOH solution at a strength of between about 2% and 10% (pH between pH 10 and pH 14.5) but preferably 5%; the suspension contains between about 0.1 and about 30% (w/w) glucan, such as 5%. A particular feature of this reaction step as discussed above, is that contrary to the known art it does not require prior exposure to strong acid or applied heat or vigorous agitation; the reaction is found to occur most advantageously at low temperatures (preferably between 2° C. to 8° C.) and with little or no mixing; the reaction time is generally between about one and twenty four hours, such as two hours. Between about 90% to 99% of the glucan particles are converted (through alkaline hydrolysis) to suspended small molecular weight molecules over the reaction time. At the conclusion of the reaction the undissolved particles are removed by standard methods such as, for example, centrifugation or filtration and the pH of the suspension adjusted the addition of Hcl (say from pH 8 to pH 10). This soluble glucan may be used as a pharmaceutical product. The glucan solution may then be adjusted to isotonicity by standard methods such as dialysis or ultrafiltration.

The glucan material produced by this method has a molecular weight range between approximately 60,000 to 250,000 with a mean of about 140,000 daltons, with a mean polydispersity index of about 2.4. Between approximately 70% and 85% of the glucan molecules are within 15% of the mean molecular weight and it is found that this result is highly reproducible with different batches. This low polydispersity index indicates relatively high homogeneity. It is thus entirely suitable for use as a pharmaceutical. It is found that this material has high biological potency, as measured, for example, in the promotion of tissue repair. In a rat dermal wound repair model, this material is approximately five times as efficacious as microparticulate Sc-glucan when compared on an equivalent molar basis (Table 6).

TABLE 6

Tensile strength of rat skin wounds (day + 7) following application of a single topical dose of 1 mg micro-particulate vs soluble Sc-glucan with 96% ($\beta$-1,3) and 4% ($\beta$-1,6) linkages.

| Treatment | n | Wound tensile strength (g) mean (SD) |
|---|---|---|
| No glucan | 12 | 196 (23) |
| Micro-particulate glucan | 14 | 356 (47) |
| Soluble glucan | 8 | 432 (69) |

In that experiment the glucans were administered in a lipophilic cream base, but it would be anticipated that this material could be used as a topical therapeutic in a variety of formulations or could be injected as a parenteral therapeutic.

In a strongly alkaline solution, the soluble glucan molecules occur principally as triple helices but with little or no polymerisation of independent helical structures. The effect of lowering the pH of the glucan solution is to predispose the glucan molecules to polymerisation leading to gel formation. At a pH below approximately 9.0 there is progressive polymerisation of adjacent helical structures. It is observed that the degree of polymerisation of the glucan molecules is related directly to the concentration of the glucan solution. Where the glucan solution is to be diluted and dispersed in a carrier vehicle and it is desirable to minimise the degree of polymerisation, the concentration of the glucan solution is generally less than 10 mg/mL, and preferably no greater than 5 mg/mL prior to adjustment of the pH from a strongly alkaline state (around pH 13). In other instances it may be desirable to have the final glucan solution as a gel and this is achieved if the concentration of the glucan solution prior to pH adjustment is greater than 10 mg/mL (10% w/w) and preferably greater than 15 mg/mL (15% w/w), for example up to about 30% w/w. It is found that this gel state is a convenient form for topical application, requiring little or no additional formulation.

It can be seen that the present manufacturing process represents a significant advance over the current state of the art in this field. Compared to other known manufacturing processes, the present process yields an end-product which has greater purity, is manufactured in a shorter time, has greater efficiency of yield, produces a glucan molecule of distinctive chemical structure, and produces a product of desired homogeneity without the necessity of elaborate and expensive separation techniques.

It readily would be appreciated that these advantages lead to considerable cost savings, with the availability of a less expensive material thus allowing wider application of Sc-glucan as a therapeutic in both veterinary and human medicine than is currently available.

The applications for which the microparticulate Sc-glucan produced by the process of the present invention are suitable include those applications in particular where the risk of direct entry of the material to the bloodstream is minimal and these include by way of example oral application, topical application, intradermal injection, intramuscular injection, subcutaneous injection, intraperitoneal injection, intrathecal injection, intralesional injection, intratendon injection, intraligament injection, intraarticular injection, and application to fracture sites of bones and cartilage. The therapeutic purposes include by way of example (a) enhancement of wound repair processes in the aforementioned tissues, (b) enhancement of resistance to infection from bacterial, fungal, viral and protozoal organisms in the aforementioned tissues, and (c) enhanced local immune responsiveness to carcinogenesis.

The applications for which the small molecular weight Sc-glucan produced by the process of the present invention are suitable include by way of example although not being limited to those listed above for microparticulate Sc-glucan: indeed in these situations the use of soluble Sc-glucan may be preferred to that of microparticulate Sc-glucan because of various practical considerations such as ease of administration or the benefit of administration in a liquid form or because of the greater bioavailability of this form. However, small molecular weight Sc-glucan has particular indication for those situations where penetration of intact tissues (such as trans-epidermal penetration of intact skin) is desired or where entry of the material to the bloodstream may occur inadvertently.

The Sc-glucans produced by the processes of the present invention can be presented in formulations commonly used in the pharmaceutical and cosmetic industries including, for example ointments, gels, suspension, emulsions, creams, lotions, powders and aqueous solutions. Glucan may be formulated with one or more carriers or excipients as are well known in the pharmaceutical art (see, for example, *Remingtons Pharmaceutical Sciences,* 17th Edition, Mack Publishing Company, Easton Pa., Ed Osol, et al, which is incorporated herein by way of reference).

Examples of carriers and excipient substances are organic or inorganic substances which are suitable for enteral (for example, oral or rectal), parenteral (for example, intravenous injection) or local (for example, topical, dermal, ophthalmic or nasal) administration and which do not react with the glucan, for example, water or aqueous isotonic saline solution, lower alcohols, vegetable oils, benzyl alcohols, polyethylene glycols, glycerol triacetate and other fatty acid glycerides, gelatin, soya lecithin, carbohydrates such as lactose or starch, magnesium stearate, talc, cellulose and vaseline.

Formulations may include one ore more preservatives, stabilizers and/or wetting agents, emulsifiers, salts for influencing osmotic pressure, buffer substances, colourants, flavourings and/or perfumes.

Glucan may be formulated into sustained release matrices which liberate glucan over time providing what may be regarded as a depot effect. Glucan in the form of a gel, as produced according to an embodiment of the aforementioned process, may be directly used as a topical pharmaceutical product or formulated with appropriate carriers and/or excipients.

In a further embodiment, this invention is directed to a glucan composition which consists essentially of branched β-(1,3)(1,6)-glucan, and which is free or essentially free of unbranched β-(1,3) glucan and non-glucan components. Reference to "essentially free" is to be understood to refer to less than about 2% unbranched β-(1,3) glucan, more specifically less than about 0.5% unbranched β(1,3) glucan.

These glucan formulations may comprise glucan in microparticulate form, soluble form or as a gel, optionally formulated or in association with one or more pharmaceutically acceptable carrier or excipients as herein described.

Glucan containing formulations or compositions for therapeutic purposes may contain from about 0.01% to about 30% (w/w), such as from about 0.1% to about 5%, more particularly from about 0.2% to about 1%, even more particularly from about 0.25% to about 0.5% (w/w). These amounts may be regarded as therapeutically effective amounts.

It has surprisingly been found by the inventors that Sc-glucan, whether produced according to this invention or by prior art processes may be used in a range of hitherto unsuspected and undescribed therapeutic applications. These applications include the treatment of ulceration or bone fracture, or the prevention/treatment of ultraviolet light induced skin damage.

In a further aspect this invention is directed to the use of glucan for the manufacture of a medicament for the treatment of skin ulceration or bone fracture, or the implantation/fixation of orthopaedic devices, or prevention/treatment of ultraviolet light induced skin damage.

In a further aspect this invention is concerned with the method for the treatment of skin ulceration or bone fracture, or the implantation/fixation of orthopaedic devices, or prevention/treatment of ultraviolet light induced skin damage, which comprises administering to a subject glucan in association with one or more pharmaceutically or veterinarily acceptable carriers or excipients.

In a still further aspect of this invention, there is provided an agent for the treatment of dermal skin ulceration, the enhancement of repair of bone and connective tissue, or the implantation/fixation of orthopaedic devices, or the prevention/treatment of ultraviolet light induced skin damage, which agent comprises glucan in association with one or more pharmaceutically or veterinarily acceptable carriers or excipients.

In these novel therapeutic uses of glucan, an effective amount of glucan is utilised. What constitutes an effective amount will depend on the particular condition being treated, mode of and form of administration, and like factors. Generally, a composition or medicament will contain glucan in an amount from about 0.05% (w/w) to about 30% (w/w), such as 0.1 to 5% (w/w), more particularly from about 0.3% to about 1% (w/w), even more particularly from about 0.25% to about 0.5% (w/w).

A particularly advantageous therapeutic application for glucan (such as microparticulate, soluble or gel forms manufactured by any of the aforementioned methods, or produced by prior art methods) according to the present invention is in the treatment of dermal ulceration. It is known that β-1,3-glucan will promote healing in full-thickness, surgically-created skin wounds in animals and humans with no dysfunctional healing, That is, the topically- or parenterally-applied glucan is able to accelerate the healing response in superficial wounds with normal healing mechanisms. It generally is assumed that glucan achieves this through activation of wound macrophages. Macrophages are critical cells in the healing process, producing a range of cytokines and growth factors which initiate the various components of the healing cascade—viz. fibroplasia, collagen production, angiogenesis, epithelialisation and collagen cross-linking. The macrophage plays a key modulatory role in this process, both initiating the process and helping to ensure that the process proceeds in a co-ordinated and integrated manner. It is assumed that a primary effect of the glucan is to produce a temporal acceleration of the healing cascade.

Dermal ulcers typically are chronic wounds which have a quite different set of physiological properties operating within the wound, compared to acute surgical wounds. Whereas the physiology of the healing process is well described for acute surgical wounds, it is ill defined for chronic ulcers. Ulcers typically show poor to negligible healing because of either constant irritation or pressure (such as decubitus ulcers or pressure sores) or restricted blood supply (such as in individuals with arterial ischaemia or venous thrombosis) or infection (such as 'tropical' ulcers) or nerve damage ('neurotrophic' ulcers) or diabetes. Ulcers have varying pathologies, and the underlying causes, where known, may be quite distinct. Various types of ulcers which may be treated according to this invention include those associated with physical trauma (radiation, thermal burns, decubitus, insect bites), impaired blood flow (arterial, venous), infection (bone, pyogenic, synergistic gangrene, syphilis, tuberculosis, tropical diseases, fungal diseases), neoplasia (primary skin tumour, metastases, leukemia) and neurotrophic lesions (spinal cord lesions, peripheral neuropathies).

Ulcers associated with dysfunctional healing vary greatly in severity, from superficial wounds extending into the dermis and having a surface area of approximately 1-2 cm$^2$ up to wounds extending through dermis, subcutaneous tissue and muscle and forming depressions and cavities with volumes of approximately 500 cm$^3$. The larger ulcers in particular can be debilitating and restrictive and require intensive and expensive therapy to manage. Control of wound sepsis, regular wound debridement, regular dressings, hypostatic drainage and corrective surgery are just some of the standard current therapies. However, currently available 'best-practice' wound management therapies are not uniformly successful, take considerable lengths of time to produce beneficial results, are associated with poor rates of patient compliance, generally are expensive, and are associated with a high incidence of ulcer recurrence. It has been noted by Margolis (J. Dermatological Surgery (1995) 21(2) 145-148) that: "a paucity of data exists that adequately addresses the efficacy of any topical agent for the treatment of pressure ulcers".

It can be seen therefore that in view of the high incidence of ulcers in the community and the cost to the community of treatment, there is an urgent need to develop improved therapies. Ideally, such a therapy should have a high rate of success, be convenient to use and produce a clinic response quickly in order to facilitate patient compliance and preferably be inexpensive.

A particular difficulty in devising a uniformly successful therapy which may be an improvement on current treatment modalities is the non-uniformity of the different types of ulcers where both the underlying aetiologic disease processes and the pathophysiology within the wounds show considerable variation. Confounding this variability, is the general poor understanding of which of the different components of the healing response is dysfunctional and therefore contributing the primary pathology of the dysfunctional healing response. So that successful antagonism of dysfunction of any particular part of the healing cascade in one ulcer type may not necessarily be successful in another ulcer type. In particular there is no evidence that local wound immune suppression or macrophage dysfunction are key pathological features or that enhancement of local immune mechanisms within such ulcers would result in enhanced healing responses as is seen in uncomplicated surgical skin wounds with no dysfunctional healing responses.

Thus it was entirely unexpected to find that topical application of glucan to decubitus, venous stasis and arterial ischaemic ulcers induced rapid and potent healing responses in those wounds. This was unexpected (a) because the primary causative factor of these ulcer types is impaired blood supply and there is no evidence to suggest that this would be responsive to antagonism by an immune stimulant, and (b) because even where it might be possible to promote the healing response, the impaired vasculature to the wound could be expected to impede the healing response as is observed with current treatment modalities. The beneficial effect of glucan in these ulcer types is even more remarkable given that a complete healing response can be achieved in the absence of other supportive therapies such as sepsis control, hypostatic drainage and correction of the primary cause.

The treatment of decubitus ulcers and venostasis ulcers are particularly preferred according to this invention, although the invention is not limited to the treatment of these ulcer conditions.

Decubitus ulcers arise through multiple mechanisms. They are a disastrous complication of immobilization. They may result from shearing forces on the skin, blunt injury to the skin, drugs and prolonged pressure which robs tissue of its blood supply. Irritative or contaminated injections and prolonged contact with moisture, urine and faeces also play a prominent role. Diminished blood circulation of the skin is also a substantial risk factor. The ulcers vary in depth and often extend from skin to a bony pressure point. Treatment is difficult and usually prolonged. Surgical techniques are at present the most important means of achieving optimal healing.

Approximately half of venous ulcers are associated with incompetent perforating veins in the region of the ankle, and constitute a long term problem in many immobile patients. Ulceration is rarely a manifestation of primary varicose veins but is virtually always associated with incompetence of the popliteal venous valve. Venostasis ulcers are most often just proximal or distal to the medial malleolus (bony ankle joint) and often develop at sites of minor trauma or skin infections. Scarring and secondary infection all impair healing and make recurrences common if healing does occur. The natural history of venous ulceration is cyclic healing and recurrence.

In the case of decubitus ulcers, the glucan preferentially is applied in the form of a powder (microparticulate glucan) or in a cream or ointment base (microparticulate, soluble or gel forms of glucan). Application is generally daily and may continue for a time period sufficient for ulcer healing, such as seven to twenty eight days. It is observed that the response to the glucan therapy is apparent clinically within 2-3 days with evidence of fresh granulation and epithelial growth. The length of time required to heal ulcers will vary according to a number of factors such as ulcer size, degree of wound sepsis and host nutritional state. Typically wound volume is reduced by 50% within 2-3 weeks with complete or near-complete wound closure effected by 4-6 weeks after commencement of glucan therapy. It is noteworthy that most of the decubitus ulcers in which glucan effects a healing response have been refractory to standard therapy including a wide range of topical preparations and wound dressings for periods up to 7 years.

In a similar manner, application of microparticulate, soluble or gel forms of glucan to venostasis and arterial ischaemic ulcers promotes ulcer healing. As with the decubitus ulcers, treatment of these ulcers with glucan leads to a clinical response in the wound within 2-3 days following the start of glucan therapy with such evidence of healing as the appearance of fresh granulation tissue and less detritus leading to a cleaner appearance in the wound. Glucan in the form of a powder, cream, lotion, ointment or gel may be topically applied to the ulcer site daily until healing occurs. The chronic nature of the underlying vascular disorder in these cases means that the predisposition to form such ulcers remains with the patient. It may be necessary therefore to continue glucan therapy on a long term basis to prevent recurrence.

It can be seen therefore that it is an entirely unexpected observation that glucan is able to promote the healing processes in skin ulcers where the individual components of the healing process are essentially normal but are unable to antagonize the dysfunctional cause such as inadequate blood supply, inadequate venous drainage, excessive tissue oedema, infection, constant pressure or other diverse causes.

It is observed that application of glucan to ulcers as described above produces a high rate of therapeutic response. Skin ulcers which either are unresponsive or poorly responsive to conventional wound management practice, typically respond within several days to treatment with glucan leading in a high proportion of cases to complete healing within several weeks of treatment. It is found that the glucan is effective in the treatment of ulcers when applied locally to the wound in various forms such as a powder, gel, cream, or dressing such as a gauze bandage or colloidal material, or any other composition generally known to those skilled in the art of pharmaceutical formulation.

In a related aspect the treatment of ulcers which respond to conventional therapies (such as normal dressings and ointments) may be accelerated with glucan administration.

Another unsuspected therapeutic application for glucan (such as, microparticulate, soluble or gel forms manufactured by any of the aforementioned methods, or other processes known in the art) according to the present invention is in the treatment of bone fracture. The repair of fractured bone characteristically is accomplished by a repair process which basically is in common with that observed in soft tissues such as skin but which differs in some important aspects. In bone, an important early step in the repair process is the formation of a fibrous structure known as a callus which bridges the fractured site providing a framework for the repair process and assuring a decree of immobilization of the fracture site. In due course the callus becomes mineralized, providing continuity with the uninjured bone and undergoes a degree of remodelling to approximate the original shape of the bone. According to this aspect of the invention the application of glucan to the site of injury enhances the rate of repair of injured bone thus facilitating fracture treatment. It is observed that the effect of such treatment is earlier induction of the callus formation and earlier organization of the connective tissue within that callus to provide a strong fibrous matrix. The result of this is the establishment of an immobilizing callus at an earlier time with the important clinical effect of reducing the risk of dissociation of the fractured edges of the bone. This is a highly desirable effect in both animals and humans because any disruption to the fracture site can predispose to delayed healing. Disruption at the fracture site remains a problem, even where methods of physical immobilization through such mechanical means as rigid splints (such as casts, bandages, etc.), or implants (such as pins, screws, etc) are used. While it is found that the process of mineralization is not appreciably enhanced by the glucan treatment, it is found that the effect of glucan in accelerating the callus phase has the effect of reducing the overall time to complete mineralization.

The glucan preferably is applied directly to the site of bone injury in a form which will maximize the retention of the glucan at the site of the fracture. Slow release formulations are well known in the art and are preferably used in these applications. It is found that the viscous gel formed by the embodiment disclosed in this invention whereby a highly alkaline soluble glucan solution at a concentration of greater than 15 mg/mL (from about 15 mg/ml to about 500 mg/ml, more preferably from about 15 mg/ml to about 30 mg/ml) is adjusted to pH 7.5 (Example 4) is a preferred form. This form is sufficiently viscous and non-miscible with blood and tissue fluids to remain at the site of application for periods up to 48 hours. An additional advantage of this gel form is that it is sufficiently tractable to be able to be injected through fine gauge needles. In this form, the glucan can be administered by injection to fracture sites where the fracture is reduced without the need for surgical exposure of the bone. Alternatively, the gel can be administered to the fracture site during open surgical reduction of fractures.

The potential usefulness of glucan treatment for human bone fractures has been evidenced in an animal model by the inventors. The rat is a standard model used in experimental medicine for bone fracture research and generally is regarded as directly predictive of human therapy (Bak et al 1992). In this animal model the inventors have established that injection of 2 mL of 15 mg/mL soluble glucan in a gel form at the site of a fractured femur resulted in accelerated healing when compared with non-treated fractures as evidenced by increased tensile strength of the partially healed bones at 12 days (Example 10).

It can thus be readily envisaged that glucan, being non-toxic and physiologically acceptable, may find wide application in fracture treatment in human and animal medicine. For example, a single bolus injection or application of glucan at the site of fracture will promote healing and increase tensile strength of the healed bone.

A further unexpected therapeutic benefit is that glucan enhances the fixture of devices such as pins, screws, artificial joints and prostheses fixed or implanted into or onto bone. It is observed that the application of glucan (such as by local application of a powder or gel, or by injection) at the site of fixation of the device enhances significantly the local inflammatory process which occurs in response to the contact of the device with bone and generally is an integral part of the strength of the bond between the bone and the device.

A particular therapeutic indication for glucan (either microparticulate or soluble forms manufactured by any of the aforementioned methods or by prior art methods) according to the present invention is in the treatment of injured connective tissues such as tendons and ligaments which has not previously been described or suggested. Such tissues are typically densely fibrous because they are subjected to relatively high stress loads. These injuries include by way of example but are not limited to (a) acute or chronic inflammation associated with over use or strain or trauma, such conditions typically being associated with sporting injuries or the syndrome known as Repetitive Strain Injury or excessive or abnormal stress, and (b) surgery, in particular where the tissue is dissected or transected. It is known that injuries of this kind in such tissues typically are slow to heal, due in part to the relative difficulty of totally resting the injured tissue because of their load bearing functions, but due largely to the characteristically lower level of activity of all aspects of the tissue healing cascade compared to that which is seen in soft tissues.

An important cause of this comparatively lower level of tissue repair activity in tendons and ligaments is a more limited blood supply compared to most soft tissues. It is found that application of glucan to the injured tendon or ligament either at the time of acute injury such as following surgery or external trauma, or with chronic injury such as chronic inflammation will promote both the rate of onset and the level of the healing response in these tissues, leading in the case of surgery to earlier return of normal strength and function and in the case of inflammation to earlier resolution of the inflammatory process. The glucan may be directly injected into the injured tendon or ligament. Although it has been described that glucan is a potent enhancer of wound repair in dermal tissue in healthy tissues, it is not apparent from that knowledge that glucan has the ability to effect enhanced resolution of chronic inflammatory processes or of enhancing repair processes in tissues with limited blood supply or where the normal rate of repair is known to be relatively slow.

A further unsuspected therapeutic indication of glucan is the prevention/treatment of ultraviolet light-induced skin damage which results from exposure to the sun.

It is well described that ultraviolet light exposure causes damage to skin, particularly long term exposure to sunlight. This is particularly the case with Caucasians who have light skin colouration which predisposes them to photo-ageing and development of certain types of skin cancers. Both of these problems are prominent within most Western communities.

The detrimental effects of sunlight are due primarily to its ultraviolet light spectrum (UV-A and UV-B). UV-B acts principally within the epidermis and rarely penetrates deeper than the uppermost layers of the dermis, while the longer wavelength UV-A penetrates through the dermal layers. The major detrimental effect of ultraviolet light is damage to proteins, particularly DNA and RNA where it results in dimer formation. Most of these dimers are repaired within several hours although a small number are either not repaired or are mis-repaired and the accumulation of these mis-repairs over a lifetime is thought to be a major contributing factor to the development of skin carcinogenesis in chronically sun-exposed individuals.

The two principal outcomes of this damage to proteins in the skin is acute cell damage and mutagenicity. Cell damage is evidenced clinically in the acute phase by the symptoms referred to generally as 'sun-burn' which include erythema (reddening) and oedema and in the long-term phase by symptoms referred to generally as 'photo-ageing' which include skin thickening and wrinkling; mutagenicity is evidenced by skin cancer development. A further effect of ultraviolet light which is not clinically apparent is immune depression. Skin has a rich network of immune cells that are equally sensitive to the detrimental effects of ultraviolet light as are other skin cells and exposure to ultraviolet light leads to temporary dysfunction of these cells. This dysfunction is repaired generally within 2-3 days but in this period the skin shows reduced immune capacity such as antigen-presentation. With repeated ultraviolet light exposure such as might be expected in individuals with a lifetime exposure to sunlight, the sun-exposed skin has chronically reduced immune function. It is likely that this predisposes to the development of skin cancer through reduced immune surveillance capacity within skin. However, the relative contributions that each of the different effects of ultraviolet light (viz. immune depression, chronic dermal and epidermal cell injury, mutagenicity) has in skin cancer development and photo-ageing remains unknown.

It has been found surprisingly by the inventors that glucan applied topically to skin either following or concomitant with ultraviolet light leads to substantial protection of the skin from ultraviolet light-induced skin damage.

This has been found in experiments conducted with a standard, hairless mouse strain used as a model to study solar damage to human skin (see, for example, Canfield et al 1985). In this model the mice are exposed daily for 10 weeks to a minimal erythemal dose of mixed ultraviolet light which simulates the toxic effects of sunlight on skin. Each daily exposure of ultraviolet light induces a mild erythema and oedema lasting up to about 24 hours and which mimics in appearance a mild 'sun-burn' in humans. With continued irradiation treatment this on-going damage is reflected in progressive thickening of the skin which histologically mimics the hyperkeratinisation and elastosis associated with photo-ageing in chronically sun-expose skin in humans. Pre-malignant tumours begin to appear within several weeks of completion of the ultraviolet light treatment regime. Over the ensuing 6-12 months there is progressive development of pre-malignant and malignant tumours, the histology and behaviour of which closely mimic the actinic keratoses and pre-malignant and non-melanoma skin cancers that develop in humans in response to sunlight.

The inventors have found that soluble glucan applied to the skin daily immediately following ultraviolet irradiation provides significant protection from both the acute toxic effects (evidenced by discernibly lesser skin erythema on each morning following the previous day's irradiation) and the chronic photo-ageing effects (evidenced by significantly thinner skin). This effect is particularly unexpected given that β-1,3-glucan is not previously known to protect tissues from direct cytotoxic damage and that there is no existing data that either confirms or suggests that β-1,3-glucan antagonises the cytochemical and histopathological lesions that are consequent to acute or chronic ultraviolet irradiation. The ability of glucan in this model to antagonise the acute toxic and chronic photo-ageing effects of ultraviolet irradiation offers a novel and important means of protection of human skin from the damaging effects of sunlight.

It also has been found by the inventors that soluble glucan applied topically to human skin immediately following exposure to sunlight affords protection from the acute erythemal effects of the ultraviolet light.

It further is found in the hairless mouse model that the glucan affords considerable protection from the development of skin cancers (see FIG. 1 hereafter). The majority of tumours at this early stage are benign sessile-based papillomas, as expected; transformation of a proportion of these to more malignant intermediate forms culminating in squamous cell carcinomas is anticipated at a later stage.

Accordingly, glucan may find wide applications in ameliorating the effects of sunlight in the human population. In this regard, the beneficial effect of glucan is obtained if it is applied either prior to, during or following sunlight exposure. To this end, it may be formulated into sunscreen formulations or into after-sun or in general cosmetic formulations such as lotions, creams and gels. The particular benefits to be gained from the use of Sc-glucan include the following: (a) amelioration of the acute toxic effects of sunlight on skin ('acute sunburn'); (b) amelioration of the chronic effects of sunlight on skin which collectively are known an photo-ageing and include symptoms such as hyperkeratinisation, skin thickening, elastosis and wrinkling; (c) amelioration of the development of sunlight-induced skin carcinogenesis.

It is to be understood that the novel therapeutic uses for glucan herein described are not limited to glucan produced by the processes described herein, although this material is preferred. Any prior glucan material such as those described by Hassid et al, Di Luzio et al, Manners et al and Jamas et al (U.S. Pat. Nos. 5,028,703, 5,250,436, 5,082,936 and 4,992,540) may be used. Preferably the glucan is Sc-glucan.

This invention will now be described with reference to the following non-limiting examples which illustrate various embodiments of the invention.

EXAMPLE 1

Microparticulate glucan is prepared as follows:

A 400 g sample of commercial *Saccharomyces cerevisiae* in dry form is added to four litres of 4% w/v sodium hydroxide and heated to 100° C. for one hour with vigorous stirring. The suspension is allowed to cool to between 45° C. and 50° C. before the lysed yeast cells are separated from the alkaline hydrolysate by centrifugation at 800 g for ten minutes. The lysed yeast cells are resuspended in a fresh batch of three litres of 3% w/v sodium hydroxide and boiled for 15 minutes. Following separation by centrifugation, the lysed yeast cells are resuspended in a fresh batch of two litres of 3% w/v sodium hydroxide and boiled for 15 minutes followed by standing at 70° C. for 16 hours. Following separation by centrifugation, the lysed yeast cells are resuspended in water and boiled for 10 minutes. The latter step is repeated once. Following centrifugation, the lysed yeast cells are resuspended in a fresh aliquot of 2 L water, the pH adjusted to 4.5 by the addition of phosphoric acid and the suspension then boiled for thirty minutes. Five hundred mL of chloroform then is added and the suspension subjected to vigorous agitation for ten minutes, following which the suspension is allowed to settle for 10 minutes in a separating funnel. The suspension separates into three distinct phases, a lower organic phase, an upper aqueous phase, and an interface between these two phases which is grey coloured. The lower chloroform phase plus a greyish intermediate phase are discarded, leaving an aqueous phase which is collected and exposed as before to a fresh batch of 500 mL of chloroform. The final aqueous phase is collected and boiled for 10 minutes to remove any residual chloroform and then dried using a spray-drier.

Analysis of the aqueous phase showed that it contained only branched β-(1,3)(1,6) glucan in the ratio of 95 to 98% β-1,3:2 to 5% β-1,6 linkages. The organic phase is slightly opaque and contains lipids but no glucan. The intermediate phase (interface) contains unbranched β-(1,3) glucan (98 to 100% β-1,3:0 to 2% β-1,6) associated within chitin, protein and other non-glucan contaminants. Biological tests showed that the branched glucan was significantly more biologically active than unbranched β(1,3) glucan in a wound healing test.

The chemical composition of glucan produced according to this invention is set forth in Table 7.

TABLE 7

| Chemical composition of Sc-glucan produced by the process of the present invention. | |
|---|---|
| | % (by weight) |
| Glucose[1] | >98 |
| Mannan[1] | <0.2 |
| Protein[2] | <0.5 |
| Glycogen[3] | <0.5 |
| Chitin[1] | <0.3 |
| Lipid[4] | not detectable |
| Glycosidic linkages:[4] | |
| β-1,3 | 96-97 |
| β-1,6 | 3-4 |

Methods of analysis:
[1] = HPLC;
[2] = Lowry method;
[3] = GC-MS;
[4] = NMR.

It is clear from this analysis that the end-product is a branched β(1,3)(1,6) glucan that is substantially pure, containing only trace amounts of impurities, and containing about 2 to 3% β-1,6 linkages.

EXAMPLE 2

Microparticulate Sc-glucan is prepared as follows:

A 400 g sample of commercial *Saccharomzyces cerevisiae* in dry form is added to four litres of 4% w/w sodium hydroxide and heated to 100° C. for one hour with vigorous stirring. The suspension is allowed to cool to between 45° C. and 50° C. before the lysed yeast cells are separated from the alkaline hydrolysate by centrifugation at 800 g for ten minutes. The lysed yeast cells are resuspended in a fresh batch of three litres of 3% w/v sodium hydroxide and boiled for 15 minutes. Following separation by centrifugation, the lysed yeast cells are resuspended in a fresh batch of two litres of 3% w/v sodium hydroxide and boiled for 15 minutes followed by standing at 70° C. for 16 hours. Following separation by centrifugation, the lysed yeast cells are resuspended in water and boiled for 10 minutes. The latter step is repeated once. Following centrifugation, the lysed yeast cells are resuspended in a fresh aliquot of 2 L water, the pH adjusted to 4.5 by the addition of hydrochloric acid and the suspension then boiled for ten minutes. Five hundred mL of chloroform then is added and the suspension subjected to vigorous agitation for ten minutes, following which the suspension is allowed to settle for 10 minutes in a separating funnel. The lower chloroform phase plus a greyish intermediate phase are discarded, leaving an aqueous phase which is collected and exposed as before to a fresh batch of 500 mL of chloroform. The final aqueous phase is collected and boiled for 10 minutes to remove any residual chloroform and then dried using a spray-drier.

The chemical composition of glucan produced according to this invention is set forth in Table 8.

TABLE 8

Chemical composition of Sc-glucan produced by the process of the present invention.

| | % (by weight) |
|---|---|
| Glucose[1] | >98 |
| Mannan[1] | <0.2 |
| Protein[2] | <0.5 |
| Glycogen[3] | <0.5 |
| Chitin[1] | <0.3 |
| Lipid[4] | not detectable |
| Glycosidic linkages:[4] | |
| β-1,3 | 98-99 |
| β-1,6 | 1-2 |

Methods of analysis:
[1] = HPLC;
[2] = Lowry method;
[3] = GC-MS;
[4] = NMR.

It can be seen that compared to the end-product material obtained in Example 1, this material has a similar degree of purity but has slightly fewer β-,6-glucan linkages indicating a lesser degree of side-branching.

EXAMPLE 3

A protocol for the preparation of minimally-polymerised, soluble Sc-glucan according to the present invention is as follows.

Microparticulate Sc-glucan is produced as detailed in Example 2. Ten g of this material is suspended in 100 mL sterile 5% NaOH solution and stirred gently for two hours at 5° C. (giving a pH around pH 13). The suspension then is diluted 1:1 in sterile, distilled water and then filtered through a 1 u membrane to remove undissolved particulate material. The pH of the filtered solution then is adjusted to 10 by the addition of 5M HCl and then dialysed against 2 L distilled water (pH 10) in a Pelicon system using a 10,000 D limiting membrane. The solution then can be sterilised by passage through a 0.45μ membrane and the pH of the solution may be adjusted as desired. The soluble glucan so produced is useful as a pharmaceutical product.

Gel permeation chromatography (Waters Styragel HR 5E® column; effective molecular weight range of $10 \times 10^4$ to $4.0 \times 10^6$ daltons) of the soluble glucan showed the material was essentially homogenous with a very narrow molecular weight spread, having an average molecular weight of 140,000 daltons and a polydispersity index of 2.564. In this determination the solvent is DMSO and the column flow rate is 1 ml/minute.

EXAMPLE 4

A protocol for the preparation of polymerised, soluble glucan according to the present invention is as follows.

Microparticulate Sc-glucan is produced as detailed in Example 2. Fifteen g of this material is suspended in 100 mL sterile 5% NaOH solution and stirred gently for two hours at 5° C. The suspension then is centrifuged at 1000 g to remove undissolved particulate material. The pH of the solution then is adjusted to 10 by the addition of 5M HCl and then dialysed against 2 L distilled water (pH 10) in a Pelicon system using a 10,000 D limiting membrane. The pH then is adjusted to 7.5 by the further addition of hydrochloric acid producing a viscous gel which is useful as a pharmaceutical product.

Gel permeation chromatography showed the material was essentially homogenous with a very narrow molecular weight spread, having an average molecular weight of 320,000 daltons and a polydispersity index of 2.2.

EXAMPLE 5

A model of delayed wound healing was developed in rats to test the ability of microparticulate Sc-glucan to promote wound healing in dysfunctional wounds. The breaking strength of seven day-old skin wounds in inbred young adult laboratory rats is determined as outlined earlier but the rats in this case are treated with drugs intended to depress the healing response. This is achieved by daily treatment from the time of wounding with a combination of prednisone (1 mg/kg), cyclosporin A (5 mg/kg) and azothioprine (2 mg/kg). This triple drug therapy provides a range of depressive effects on macrophages, lymphocytes and vascular endothelium.

Table 9 summarizes the results of the use of Sc-glucan in this model. The effect of the triple drug therapy was to reduce significantly ($p<0.01$) the breaking strength of the wound at seven days. A single application of 1 mg of microparticulate Sc-glucan (per 5 cm linear length skin wound) produced by the process of the present invention successfully antagonized the depressive effect of the triple drug therapy, returning the breaking strength of the wound to that seen in normal immunocompetent rats.

TABLE 9

Effect of topical Sc-glucan therapy on the breaking strength of skin wounds in rats with and without drug-induced depressed wound healing.

| Group | Drug treatment | Glucan treatment | Wound breaking strength (g) (mean) |
|---|---|---|---|
| 1 | None | None | 422 |
| 2 | Yes | None | 275 |
| 3 | Yes | Yes | 442 |

EXAMPLE 6

Glucan Formulations

A topical preparations for human and veterinary applications were prepared from the following components:

| TOPICAL CREAM | | |
|---|---|---|
| β-1,3-glucan (microparticulate) | BP | 1 mg/g |
| Zinc stearate | BP | 3 mg/g |
| Cetomacrogol 1000 | BP | 20 mg/g |
| Cetostearyl alcohol | BP | 80 mg/g |
| Phenoxyethanol | BPC 1973 | 5 μL/g |
| Glycerol | BP | 60 mg/g |
| Arachis oil | BP | 40 mg/g |
| Purified water | BP | to 1 g |

This formulation may be referred to as Formulation #1.

A powder for topical application was prepared from the following components:

| TOPICAL POWDER | | |
|---|---|---|
| β-1,3-glucan (microparticulate) | | 100 mg/g |
| Maize corn flour | BP | 900 mg/g |

This formulation may be referred to as Formulation #2.

A topical cream was prepared by mixing the following components:

| TOPICAL CREAM | |
|---|---|
| Paraffin oil | 80 ml |
| Olive oil | 60 ml |
| Anhydrous lanolin cetomacrogol 1000 | 60 g |
| Stearic acid Cetostearyl alcohol | 58 6 |
| Glyceryl monostearate phenoxyethanol | 60 g |
| Oleic acid glycerol | 25 ml |
| Water | 1200 ml |
| Triethanolamine | 27 ml |
| Soluble glucan of Example 3 | 20 ml |

This formulation may be referred to as Formulation #3 and provides a cream containing 5 mg soluble glucan per g.

Formulations #1 to #3 were varied by incorporating glucan in the form of a gel. These may be referred to as Formulations #1A to #3A.

EXAMPLE 7

A decubitus ulcer was treated successfully in a human patient using Formulation #1.

The patient was a ninety year old male stroke victim who had been hospitalized for ten years and who was essentially bed-ridden. A decubitus ulcer had developed on the right buttock in 1986 and persisted despite regular medical and nursing attention. By 1988 the ulcer had grown to a diameter of 8 cm and to a depth of 4 cm. Conventional treatments consisting of regular wound cleansing, application of protective dressings and body positioning to minimize pressure to the ulcer had failed to halt the progressive deterioration of the ulcer.

Treatment with Sc-glucan was commenced and involved topical application using Formulation #1. Daily topical treatments were carried out for one week and then ceased. Two weeks after treatment the ulcer was totally healed; epithelialization was complete and there was no visible scar formation.

EXAMPLE 8

A patient (Mr G W) suffering from persistent leg ulcers was treated with glucan (Formulation #1).

The patient was a fifty three year old male who suffered a sporting injury which included a fractured ankle. Following this injury the ankle was reconstructed twice. After the second reconstruction the wound did not heal and four venostasis ulcers developed despite the use of systemic and topical bactericides and antibiotics.

Following five successive daily applications of the glucan containing formulation 1 wound healing cream of Example 5 to three of the ulcers, one originally measuring 3.8 cm×1.9 cm completely healed in ten days; one measuring 10.2 cm×3.8 cm was reduced to 6.3 cm×1.3 cm during the ten day treatment period; and a further ulcer measuring 3.8 cm×1.9 cm was reduced to 2.5 cm×1.2 cm. The treatment was recommenced on the tenth day and after two further cycles of treatment comprising cream application for seven days and no treatment for seven days the latter two ulcers completely healed after four weeks. Treatment of the fourth ulcer (10 cm×9 cm) involving two exposed tendons and extensive tissue necrosis was commenced shortly thereafter. After ten days of daily treatment, there was clear evidence of epithelial regrowth and granulation tissue leading to coverage of the exposed tendons by granulation tissue and overall reduction in wound size to 8 cm×7 cm.

The patient had never observed such positive results from any previous treatment.

EXAMPLE 9

The posterior aspect of the forearm of a six year old thoroughbred stallion was severely traumatized in a fight with another stallion creating a deep cavity with an external hole some 40 cm×20 cm in area. Initial treatment was irrigation with disinfectant and antibiotic solutions but after several days the severity of the injury became more apparent and appeared to be worsening. There was extensive and deep sloughing occurring with necrosis of deep tissues including ligament and tendons and associated muscle masses—some tendon remnants were present as unhealthy looking strands and the animal could not bear weight. The affected area was treated at that time by topical application of Formulation #1 of Example 5.

There was an immediate and profound response to glucan treatment.

The sequence of the clinical response to treatment was as follows:

24 hr post-treatment: Necrosis lessened with reduction in suppuration.

36 hr post-treatment: Marked improvement in appearance of wound with tissue showing vitality.

72 hr post-treatment: Whole area filling in rapidly with ligament and tendon remnants being included in new tissue.

96 hr post-treatment: General appearance of good rapid healthy healing with peripheral epithelialization evident.

The wound ultimately completely closed after 12 days of treatment and with minimal scarring.

The animal at that time was weight-bearing on all legs.

EXAMPLE 10

Four adult rats (male, Wistar, inbred) had their left femurs broken under anaesthesia using externally-applied force. The fracture site was located by external palpation and a 21-gauge needle then introduced through the skin over the fracture site and positioned between the fractured ends of the femur. The fracture then was immobilised in the standard way by insertion of an intra-medullary pin through the knee joint to emerge through the femoral head. In two rats, 2 mL of colloidal glucan produced as per Example 4 were injected into the fracture site via the previously-positioned needle. In the other two rats, 2 mL of saline was injected instead of glucan.

The needle then was withdrawn and the rats allowed to recover from the anaesthetic. Twelve days later the rats were killed, the intra-medullary pins removed and the fractured femurs isolated for visualisation of the fracture site and determination of the strength of the healing response. In the two control (saline) rats, the fracture site was contained within a rudimentary callus and was able to be displaced readily by torsion of the upper and lower femoral shafts. In the two glucan-treated rats, the callus was further advanced, being firmer and considerably greater force was required to displace the fractured ends of femur. It was concluded that the effect of the glucan had been to accelerate callus formation, leading to a firmed bond of the fracture site at 12 days post-fracture.

EXAMPLE 11

A 50 year-old Caucasian male exposed an area of skin approximately 4 cm×12 cm on the inner aspect of both forearms to direct sunlight for a period of 40 minutes. Both areas were exposed under identical conditions and both forearms had similar levels of skin pigmentation. Each exposed area was divided into 4 equal patches (4 cm×3 cm) which were delineated by indelible ink. On each forearm, 1 gm of sun-cream (SPF 10) was applied to one of the end patches prior to sun-exposure; the remaining patches were untreated at this time. Two hours following sun-exposure Sc-glucan (Formulation #3 from Example 6) was applied to the second patches, the third patch was left untreated, and 2 gm of Formulation #3 (Example 6) base without Sc-glucan applied to the fourth patch. The order of treatment was reversed on each forearm.

The skin patches were examined 24 hours following sun-exposure and the degree of redness assessed visually by scoring 0, +, ++, +++ and ++++. The results were as follows:

| | |
|---|---|
| untreated | ++++ |
| SPF 10 | + |
| cream base only | ++++ |
| glucan + cream base | ++ |

The glucan effected considerable reduction of skin redness. Hence, glucan ameliorated the clinical response to sun damage.

EXAMPLE 12

Albino Skh:HR-1 hairless mice were irradiated daily with U.V. light for a period of 12 weeks. After each daily irradiation, mice were painted with glucan cream of (Formulation #3), cream base alone or untreated. Results are shown in Table 10.

TABLE 10

Mean no. of pre-malignant (papillomas, hyperkeratoses, kerato-acanthomas) and malignant (carcinomas) in albino Skh: HR-1 hairless mice, following 12 weeks ultraviolet irradiation painted with 0.1 ml of either cream base lotion or Sc-glucan (7 mg/day) and cream base each day.

| | | Mean no. skin tumours per mouse Weeks | | | | |
|---|---|---|---|---|---|---|
| Treatment | no. mice | 11 | 14 | 17 | 19 | 21 |
| Cream base only | 20 | 0 | 1.762.7 | 4.763.9 | 7.663.9 | 13.368.3 |
| Sc-glucan + cream base | 20 | 0.0560.2 | 0.0560.2 | 0.9561.9 | 1.762.6 | 4.664.7* |

*p = 0.004

Mice irradiated by UV painted with neither Sc-glucan and cream base, or cream base alone, registered as many tumors as mice painted with cream base alone (data not shown).

EXAMPLE 13

Mice are exposed daily for ten weeks to a minimal erythemal dose of U.V. light which stimulates the toxic effects of sunlight on skin. Each daily exposure of U.V. light induces a mild erythema and oedema lasting up to 25 hours which mimics a mild 'sun-burn' in humans. Mice were either treated with Formulation #3 after U.V. light exposure (group 1) or treated with base lotion containing no glucan (group 2). At six weeks notable skin thickening (and consequential wrinkling) was observed for group 2 mice. Mice of group 1 were largely protected from these effects. Erythema was not observed in group 1 mice over the treatment period. FIG. 1 depicts the results obtained in one test. After 6 weeks, glucan treated mice (-□-) showed appreciably less skin fold thickness than untreated mice (-◇-).

REFERENCES

Bacon J S D, Farmer, V C, Jones D, Taylor I F, "The glucan component of the cell wall of baker's yeast (*Saccharomyces cerevisiae*) considered in relation to its ultrastructure", *Biochem. J.*, 114, 557-567 (1969)

Bak B, Jensen K S, "Standardization of Tibial Fractures in the Rat" *Bone*, 13, 289-295 (1992)

Canfield P J, Greenoak G E, Reeve V E, Gallagher C H, "Characterisation of UV induced keratoancanthoma-like lesions in HRA/Skh-1 mice and their comparison with keratoacanthomas in man", *Pathology*, 17(4), 613-616 (1985)

Cook J A, Holbrook T W, Parker B W, "Visceral leishmaniasis in mice: protective effect of glucan", *Journal of the Reticuloendothelial Society*, 27, 567-573 (1980)

Czop J K, Austen K F, "Generation of leukotrienes by human monocytes upon stimulation of their β-glucan receptor during phagocytosis", *Proceedings of the National Academy of Sciences (USA)*, 82, 2751-2755 (1985)

Di Luzio N R, Williams D L, McNamee R B, Edwards B F, Kitahama A. "Comparative tumor-inhibitory and antibacterial activity of soluble and particulate glucan", *Int J Cancer*, 24, 773-779 (1979)

Deimann, Fahimi, *Journal of Experimental Medicine*, 149, 883-897 (1979)

Hassid W Z, Joslyn M A, McCready R M, "The molecular constitution of an insoluble polysaccharide from yeast, *Saccharomyces cerevisiae*", *Journal of the American Chemical Society*, 63, 295-298 (1941)

Kelly G E, Lui, W, "Accelerated wound healing in normal and immunosuppressed animals", *Norvet Research Pty Ltd*, 1994, Report G94003.

Maeda Y Y, Chihara G, "The effects of neonatal thymectomy on the antitumour activity of lentinan, carboxymethylpachymaran and zyrnosan, and their effects on various immune responses", *International Journal of Cancer*, 11, 153-161 (1973)

Manners D J, Masson A J, Patterson J C, "The structure of a β-(1,3)-D-glucan from yeast cell walls", *Biochem J*, 135, 19-30 (1973)

Mansell P W A, Ichinose H, Reed R J, Krementz E T, McNamee R, Di Luzio N R, "Macrophage-mediated destruction of human malignant cells in vivo", *Journal of the National Cancer Institute*, 54, 571-580 (1975)

Niskanen, *Cancer Research*, 38, 1406-1409 (1978)

Patchen, Lotzova, *Experimental Haematology* 8, 409-422 (1980)

Riggi S, Di Luzio N R, "Identification of a RE stimulating agent in zymosan", *American Journal of Physiology* 200, 297-300 (1961)

Sherwood E R, Williams D L, Di Luzio N R, "Glucan stimulates production of antitumor cytolytic/cytostatic factor(s) by macrophages", *Journal of Biological Response Modifiers*, 5, 504-526 (1986)

Sherwood E R, Williams D L, McNamee R B, Jones E L, Browder I W, Di Luzio N R, "Enhancement of interleukin-1 and interleukin-2 production by soluble glucan", *International Journal of Immunopharmacology*, 9, 261-267 (1987)

Williams D L, Pretus H A, McNamee R B, Jones E L, Ensley H E, Browder I W, Di Luzio N R, "Development, physicochemical characterization and preclinical efficacy evaluation of a water soluble glucan sulfate derived from *Saccharomyces cerevisiae*" *Immunopharmacol*, 22, 139-156 (1991)

Williams D L, Cook J A, Hoffmann E O, Di Luzio N R, "Protective effect of glucan in experimentally induced candidiasis", *Journal of the Reticuloendothelial Society* 23, 479-490 (1978)

Williams D L, Browder I W, Di Luzio N R, "Immunotherapeutic modification of *E. coli*-induced experimental peritonitis and bacteremia by glucan", *Surgery*, 93, 448-454 (1983)

Williams D L, Sherwood E R, McNamee R B, Jones E L, Di Luzio N R, "Therapeutic efficacy of glucan in a murine model of hepatic metastatic disease", *Hepatology*, 5, 198-206 (1985)

Williams D L, McNamee R B, Jones E L, Pretus H A, Ensley H E, Browder I W, Di Luzio N R, "A method for the solubilization of a (1-3)-β-D-glucan isolated from *Saccharomyces cerevisiae*", *Carbohydrate Research*, 219, 203-213 (1991)

The references referred to herein are incorporated by reference.

The invention claimed is:

1. A method of treating a dermal ulcer of a subject, comprising applying topically a glucan composition to a dermal ulcer of a subject, wherein said glucan composition comprises an effective amount of a water insoluble microparticulate β-(1,3)(1,6) glucan, thereby treating a dermal ulcer of a subject.

2. The method of treatment according to claim 1 wherein said glucan composition further comprises one or more pharmaceutically acceptable carriers or excipients.

3. The method of treatment according to claim 1 wherein said glucan composition is in the form of a powder, cream, lotion, ointment or gel.

4. The method of treatment according to claim 1 wherein the dermal ulcer is caused by at least one of constant irritation and pressure.

5. The method of treatment according to claim 1 wherein the dermal ulcer is any one or more of decubitus, venous stasis, or a pressure sore ulcer.

6. The method of treatment according to claim 1 wherein the dermal ulcer is caused by restricted blood supply.

7. The method of treatment according to claim 6 wherein the restricted blood supply is caused by at least one of arterial ischaemia and venous thrombosis.

8. The method of treatment according to claim 1 wherein the dermal ulcer is caused by infection.

9. The method of treatment according to claim 8 wherein the infection is caused by at least one of bone infection, pyogenic infection, synergistic infection, gangrene, syphilis, tuberculosis, tropical diseases, and fungal diseases.

10. The method of treatment according to claim 1 wherein the dermal ulcer is caused by nerve damage.

11. The method of treatment according to claim 10 wherein the nerve damage is caused by at least one of spinal cord lesions and peripheral neuropathies.

12. The method of treatment according to claim 1 wherein the dermal ulcer is caused by neoplasia.

13. The method of treatment according to claim 12 wherein the neoplasia is caused by at least one of primary skin tumor, metastases, and leukemia.

14. The method of treatment according to claim 1, wherein the ratio of β-(1,3) to β-(1,6) linkages is from 90 to 98% β-(1,3) linkages and from 2 to 10% β-(1,6) linkages.

15. The method of treatment according to claim 1 wherein the dermal ulcer is associated with dysfunctional healing.

16. The method of treatment according to claim 1 wherein the effective amount of a water insoluble microparticulate β-(1,3)(1,6) glucan in the glucan composition is about 0.3% to about 1% (w/w) water insoluble microparticulate β-(1,3)(1,6) glucan.

17. The method of treatment according to claim 1 wherein the effective amount of a water insoluble microparticulate β-(1,3)(1,6) glucan in the glucan composition is about 0.25% to about 0.5% (w/w) water insoluble microparticulate β-(1,3)(1,6) glucan.

* * * * *

UNITED STATES PATENT AND TRADEMARK OFFICE
CERTIFICATE OF CORRECTION

PATENT NO. : 7,648,968 B2
APPLICATION NO. : 11/499904
DATED : January 19, 2010
INVENTOR(S) : Graham Edmund Kelly It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 339 days.

Signed and Sealed this

Twenty-third Day of November, 2010

David J. Kappos
*Director of the United States Patent and Trademark Office*